United States Patent [19]

Bruzzese et al.

[11] Patent Number: 5,296,597
[45] Date of Patent: Mar. 22, 1994

[54] AMIDE DERIVATIVES OF PARTRICIN A & PARTRICIN B

[75] Inventors: Tiberio Bruzzese; Franco Ottoni; Giuseppe Ghielmetti, all of Milan, Italy

[73] Assignee: SPA Societa' Prodotti Antibiotici S.P.A., Milan, Italy

[21] Appl. No.: 612,912

[22] Filed: Nov. 14, 1990

[30] Foreign Application Priority Data

Nov. 16, 1989 [IT] Italy ................. 22396 A/89

[51] Int. Cl.$^5$ ........................................... C07D 265/30
[52] U.S. Cl. ................................. 544/106; 544/358; 546/148; 424/122; 536/6.5; 548/400; 564/191
[58] Field of Search .............. 544/106, 358; 424/122; 536/6.5; 546/148; 548/400; 564/191; 514/31

[56] References Cited

U.S. PATENT DOCUMENTS 3,961,047  6/1976  Bruzzese et al. ................. 424/122
4,783,527  11/1988  Falkowski et al. ................. 536/6.5

OTHER PUBLICATIONS

Cyerwenski, A., et al, Journal of Antibiotics, vol. 40, #7, pp. 1023-1027 (1987).
Merck Index, 11th Ed, pp. 5733, 5734, 6997, 6998 (1989).
Tweit et al, J. of Antibiotics, vol. 35, pp. 997-1012 (1982).
Martindale The Extra Pharmacopoeia, 29th Ed, The Pharmaceutical Press, London, pp. 416-420 (1989).
Jarzebski et al, J. of Antibiotics, vol. 35, pp. 220-229 (1982).

Primary Examiner—José G. Dees
Assistant Examiner—D. D. Carr
Attorney, Agent, or Firm—Oblon, Spivak, McClelland, Maier & Neustadt

[57] ABSTRACT

The present invention is directed towards a series of secondary and tertiary amide derivatives of Partricin A & Partricin B attached at the C-18 carboxyl group. The compounds can be used in the treatment of hypercholesteremia and hyperlipemia conditions, of steroidal imbalances, and as antifungal and antiprotozoan agents.

25 Claims, No Drawings

AMIDE DERIVATIVES OF PARTRICIN A & PARTRICIN B

Partricin is an antibiotic substance from the subgroup of aromatic heptaenes having polyene macrolide structure, the formula of which is shown in the Merck Index, 10th Ed., n. 6909. The product was isolated from the fermentation broths of the *Streptomyces aureofaciens* strain NRRL 3878 and is claimed, for example, in our G.B. Pat. 1,357,538.

Further studies have shown that partricin comprises two components, called partricin A and B, in a ratio of about 1:1, that have been separated by means of various techniques, such as the countercurrent chromatography according to Craig, or have been synthesized directly and are characterized, as the sole structural difference, by a methylamine group (partricin A) or an amine group (partricin B) on the aromatic nucleus in the C-37 side chain.

From the point of view of the biological activity, partricin exhibits a very high antimycotic activity—especially on yeasts, such as *Candida albicans*—and antiprotozoan activity. Said activity is due to its interaction ability with sterols (especially ergosterol) of the cell wall, that are therefore the target of its antimicrobial action. In other works on experiamental animals, it has been shown that partricin is active in hypercholesteremia and prostatic hypertrophic conditions, both activities being essentially due to its cholesterol complexing ability. Said biological effects are shown, almost in the same degree, by both partricin A and partricin B, that in fact have similar chemical structure and biological activity. Partricin exhibits however, like the other natural polyenes, many drawbacks: the low interaction selectivity with ergosterol in the fungal cell and with cholesterol in the animal cell involves a low action selectivity and gives rise to many toxic effects in human (hemolytic action, renal function and cell damage, systemic toxic effects, and so on). Moreover, the low or almost absent water solubility, which is a common characteristic of all the polyenes, prevents from preparing injectable formulations, drastically reduces the biovalability after the oral administration, and is a strong hindrance to diffusion after topic application.

To solve said difficulties, many partricin derivatives have already been prepared (see U.S. Pat. No. 3,961,047), the most promising of which (methyl ester or mepartricin USAN) has been claimed by the present applicants in U.S. Pat. No. 3,780,173.

Said derivative shows in fact a greater action selectivity, an increased antimycotic activity and reduced toxicity, but still exhibits marked toxic effects and, consequently, apart for the topic application, a low clinical manageability in other therapeutical uses. It has also been noticed that to the esters of other polyenes, such as amphotericin B methyl ester, severe neurotoxic effects are ascribed: it is not yet know whether said effects are due to the compound per se or, rather, to specific by-products that are formed as a consequence of the known reactivity of diazomethane and other diazoalkanes used in the esterification processes, but this is anyway a potential risk factor in the preparation of esters of other polyenes, included partricin.

Mepartricin also exhibits, like the starting material, an insufficient water solubility and must therefore be complexed with surfactant, such as sodium lauryl sulfate (see our U.S. Pat. No. 3,961,048) to obtain injectable solutions for parenteral use or to improve the bioavalability after oral administration: in this case too, however, there are not obtained true molecular solutions, but only pseudosolutions or water dispersions in micelle form; moreover, the concurrent administration of the surfactant agent increases the undersirable toxic effects (hemolysis, hepatic toxicity, and so on) after the intravenous application. It is therefore absolutely necessary to search new derivatives. We have now prepared a new series of derivatives having an amine structure, and their salts, starting both from partricin and from its components A and B, said new derivatives apparently having markedly better biological activity and physicochemical characteristics.

The structure of the amides that are the object of the present invention is schematically shown in general formula I

wherein:

R represents the residue of the partricin (or partricin A or partricin B) molecule, which is bound to the C-18 carboxyl;

$R_1$ represents an alkyl group having 1 to 12 carbon atoms, an alkenyl group having 2 to 6 carbon atoms, a cycloalkyl group having 3 to 6 carbon atoms or a phenyl group; or stands for a dimethylamino-substituted cyclohexyl or phenyl group; or for an alkyl group with 1 to 6 carbon atoms substituted with an N-methyl- or N-ethyl-cycloalkyleneamine with 4 to 5 carbon atoms, with a pyridyl group or with a primary amine group $NH_2$, a secondary amine group $NHR_3$ or a tertiary amine group $NR_3R_4$, $R_3$ and $R_4$ being alkyls with 1 to 4 carbon atoms, or $NR_3R_4$ together form a basic nitrogen heterocycle, said heterocycle being 5- or 6-membered and optionally containing one or more further heteroatoms chosen from N—preferably in the form of $N(CH_3)$ or $N(CH_2CH_2OH)$— or O or S;

$R_2$ represents a hydrogen atom or has the same meanings as $R_1$; or $NR_1R_2$ together form a basic nitrogen heterocycle, said heterocycle being 5- or 6-membered and optionally containing one or more further heteroatoms chosen from N—preferably in the form of $N(CH_3)$ or $N(CH_2CH_2OH)$— or O or S;

n is an integer of from 0 or 2,

X is the residue of a pharmacologically and pharmaceutically acceptable organic or inorganic acid.

The compounds of formula I have been prepared by reacting the C-18 carboxyl of partricins R—COOH (II) with suitable amines $NHR_1R_2$ (III), using diphenyl phosphorazidate $(C_6H_5O)_2PON_3$ as condensing agent, having an activating action on the carboxyl groups through the formation of the corresponding amides already known from literature, and optionally in the presence of triethyl amine. The reaction has been carried out in dimethyl acetamide or other inert dipolar solvents that can dissolve the starting antibiotic, without using any protective group the polyfunctional character of the polyene notwithstanding, and using, on the contrary, a great excess of the various reagents. After 1-12 hours of reaction at a temperature of between 0° and 50° C., usually at ambient temperature, according to the results of a thin layer chromatography control, the raw product was precipitated by means of suitable organic solvents and collected by filtration. The final purification of the various amines was then carried out by means of solubilization and reprecipitation with usual solvents, or by means of silica gel column chromatography.

Also to counter-current partition according to Craig can be used to remove the impurities and, in the case of the partricin amides, to separate the A and B components. The final control of the products thereby obtained can be carried out by means of the usual techniques: elementary analysis, LTC, IR, mass spectrometry, ultraviolet spectrometry, (the ultraviolet spectrum being qualitatively unchanged as compared to the starting product), retention time and purity determination by means of high pressure liquid chromatography (HPLC).

The amides thereby obtained are yellow solids with high, not well defined melting points (gradual decomposition), that are soluble in dipolar organic solvents, such as dimethyl sulphoxide, dimethyl formamide, dimethyl acetamide, and so on, scarcely soluble in the usual organic solvents, very little soluble in water. Consequently, many amides—especially those substituted with basic groups—have advantageously been transformed into the related salts with organic or inorganic, non toxic, pharmacologically acceptable acids, such ascorbate, aspartate, glutamate, hydrochloride, and so on, or especially glucuronate and glycolate, all the salts being moderately to strongly water soluble and having an approximately neutral, or only slightly acidic pH.

The salts can be easily prepared, for example, by suspending the amide in water, adding 1–2 equivalents of acid and evaporating then to dryness the solution thereby obtained (under vacuum and at a reduced temperature) or by liophilization. Alternatively, the salt can be isolated by precipitation from the water solution by means of suitable organic solvents.

As far as the microbiological activity of the amide derivatives or partricin is concerned, many among them are more active or at least as active as the starting products, as can be seen from some illustrative examples in table I. A similar or even higher activity is exhibited by the partricin A and partricin B amides.

The activity on yeasts has been studied in particular on the *Candida albicans* strain No. 36 (SPA collection, (Milan)), with the method of the minimum inhibitory concentration (MIC) in a liquid medium (Fluid Sabouraud Medium, Difco) and in a solid medium, obtained by adding 15% agar (Difco) to the former medium, with an incubation time of 24 hours at 36° C.

The substituted amides with short, saturated or unsaturated aliphatic chains (methyl, ethyl, allyl), especially those further substituted with basic groups, have all been shown to be much more active then the starting products. Little difference, on the contrary, has been found between the corresponding derivatives of partricin A and B.

A similar result has been obtained by determining the product concentration ($IC_{50}$) that reduces by 50% the growth (turbidimetric determination) of a *Saccharomyces cerevisiae* culture after 6 hours of incubation at 60° C. in PYG medium; the short chain amides and the basic amides have shown, in the average, $IC_{50}$ values that are 5–10 times lower than those of the unreacted polyene.

The activity on protozoa, in particular on *Trichomonas vaginalis* strain No. 6 (SPA collection, Milan) has been determined by means of the minimum inhibitory concentrations (MIC) in CPLM medium with 72 hours incubation at 36° C., and the activity of the methyl amides has been shown to be almost unchanged, or only slightly reduced, related to the starting partricins.

A further important evaluation parameter was the helomytic power: rat erytrocytes were suspended at a 2% concentration in Ringer solution containing 0.2% of bovine serum albumin, fraction V (BSA) and incubated for 1 hour at 36° C. in the presence of various amounts of the amides being investigated. The polyene concentration that causes hemoglobin liberation of 50% of the total amount ($EC_{50}$) was then determined by means of centrifugation of the intact erythrocytes and reading the supernatant absorbance at 540 nm with a colorimeter. The amides having a greater antimycotic activity, such as the methyl amide, 2-dimethylaminoethyl amide, 3-dimethylaminopropyl amide, have been shown in this test to be about 25–80 times less hemolytically active then unreacted partricins. This result seems to be highly relevant as the hemolytic power of the polyene (or of drugs generally) is clearly related to its systemic toxicity.

In any case, it is an evident indication of the affinity to the animal cell membranes.

The discovery of polyene derivatives more antimycotically potent (and therefore exhibiting a higher complexing capacity for the fungal wall ergosterol) and less hemolytically active, that is exhibiting a lower affinity to the red blood cell cholesterol, is a good starting point for the obtainment of a drug with a highly selective action (greater activity, lower toxicity). Said substance will then find application (more advantageously relative to partricin—which is not used for clinical application—and to mepartricin) also in other therapeutical fields where much longer treatments are required then in the antiinfectious therapies and where, consequently, much better tolerated drugs are needed, for example in the treatment of hypercholesteremia and hyperlipemia conditions and of steroid hormones unbalances, in the therapy of hypertrophic prostate, in the potential use as immunostimulating agents; or when higher dosages are anticipated, such as in the infections caused by potentially sensible viruses, for example those having a lipid envelope.

As for the salts of the above-mentioned amides, especially the most basic ones, they are much more water soluble, as already explained, and therefore do not need to be complex-bound with surface active substances. They provide in fact aqueous solutions that exhibit a well resolved ultraviolet spectrum with very marked absorption maxima at 342, 360, 380 and 402 nm (conc. 10 mcg/ml), said behavior being typical of the true molecular solutions.

UV spectra of the same kind are in fact obtained when non water-soluble polyenes are dissolved in organic solvents, whilst the spectrum is shifted to longer wavelengths, with a low resolution of the absorption maxima and lowered molecular absorbance, when the water solubility is obtained by adding surface active agents: in this case pseudosolutions or colloidal solutions are obtained in which the dissolved substance is aggregated to micelles.

The salts of the present invention obviously exhibit the whole spectrum and potency of the free amides and their possible therapeutical applications in a full degree. The possibility of obtaining water solutions without adding foreign surface active substance makes them especially suited for the preparation of injectable solutions as required in the treatment of severe fungal and protozoan systemic infections. The water solubility feature potentially enhances also the bioavailability after oral administration, for which, if necessary, suitable gastric formulations to the purpose of avoiding the contact with the highly acidic gastric juice, that might degrade the active ingredient, can be used.

For all the therapeutical uses, the compounds can be diluted with suited amounts of a solid or liquid pharmaceutically acceptable vehicle. The preparations comprise tablets, tablets resistant to the gastric environment, effervescent tablets, powders, granules and capsules, as well as suspensions and solutions in oily or aqueous vehicles, all said preparations being suitable for oral use.

It is also possible to formulate the active ingredient as cremes and ointments for dermatologic use, or as suppositories and vaginal candles or tablets for topic use.

Alternatively, the compounds can be administered by the parenteral route by using sterile aqueous solutions or, preferably, lyophylized powders to be solubilized at the moment of use. Even more than in the other formulations, in the injectable formulations the compounds are used in the form of water soluble salts.

In any case it is possible to formulate the compounds together drugs, depending on the conditions to be treated therapeutically.

The following examples are provided to further illustrate the present invention, but should not be construed as limiting the invention.

EXAMPLE 1

To a solution of 6.6 g of partricin A in 55 ml of dimethyl acetamide, there are added at room temperature, under stirring, 0.89 g of methyl amine (dissolved in 10 ml of dimethyl acetamide), followed by 2.9 g of triethyl amine and 7.9 g of diphenyl phosphorazidate.

The mixture is then stirred at room temperature for 4 hours, checking the progress of reaction by thin layer chromatography.

At the end, the reaction mixture is treated with 500 ml of an ether:ethanol 9:1 mixture and the precipitate thereby obtained is filtered off, washed with ether and dried at 40° C. under vacuum, thereby obtaining 5.8 g of product. The crude substance is then purified by means of a suitable solvent mixture or by counter-current partition, or preferably by means of column chromatography on silica gel, eluting with methylene chloride:methanol:diethylamine:water, in the ratio 86:10:4:1. After TLC assay, the suitable eluate fractions are evaporated to dryness under reduced pressure to give the required partricin A methyl amide (2.1 g) as a yellow-coloured crystalline solid.

Analysis: the structure and purity of the compound are tested, besides the IR and UV spectrometry, also by means of elementary analysis, thin layer chromatography (TLC) and high resolution liquid chromatography (HPLC).

The TLC analysis is carried out on silica gel 60F254 plates (Merck), eluting with dichloroethane:ethanol:40% dimethylamine in H₂O in the ratio 64:30:9 with UV detection ($\lambda$ =254 nm).

The HPLC analysis is carried out by means of a Perkin-Elmer series 3 (or Hitachi Mod. L6200) chromatograph; Hibar Lichrocart 125 mm column, diameter 4 mm, packed with Superspher RP-18 4$\mu$; room temperature; 2 pumps with gradient programming, constant flow-rate of 1 ml/min.; solvent system, acetonitrile and 0.005M EDTA aqueous solution; isocratic (35% acetonitrile, 15 min.), gradient curve 2 (65% acetonitrile, 45 min.), linear gradient (80% acetonitrile, 10 min.), re-equilibration (35% acetonitrile, 10 min.); spectrophotometer at 378 nm, cell 8$\mu$×1 cm.

Elem. anal.: for $C_{60}H_{89}N_3O_{18}$. Found %: C 63.25; H 7.85; N 3.67. Calc. %: C 63.19; H 7.87; N 3.68.

TLC, Rf 0.45

HPLC, retention time 32.1 min.

EXAMPLE 2

Operating essentially in accordance with the procedure of example 1, the following compounds have been prepared:

Partricin A ethyl amide

Elem.anal.: for $C_{61}H_{91}N_3O_{18}$. Found %: C 63.52; H 7.93; N 3.66. Calc. %: C 63.47; H 7.95; N 3.64.

TLC, Rf 0.53

HPLC, retention time 36.6 min.

Partricin A n-propyl amide

Elem.anal.: for $C_{62}H_{93}N_3O_{18}$. Found %: C 63.08; H 8.15; N 3.63. Calc. %: C 63.73; H 8.02; N 3.60.

TLC, Rf 0.58

HPLC, retention time 41.2 min.

Partricin A n-pentyl amide

Elem.Anal.: for $C_{64}H_{97}N_3O_{18}$. Found %: C 64.86; H 8.19; N 3.49. Calc. %: C 64.25; H 8.17; N 3.51.

TLC, Rf 0.69

HPLC, retention time 49.2 min.

Partricin A allyl amide

Elem.anal.: for $C_{62}H_{91}N_3O_{18}$. Found %: C 63.92; H 7.99; N 3.58. Calc. %: C 63.84; H 7.86; N 3.60.

TLC, Rf 0.58

HPLC, retention time 46.2 min.

Partricin B methyl amide

Elem.anal.: for $C_{59}H_{87}N_3O_{18}$. Found %: C 63.10; H 7.88; N 3.76. Calc. %: C 62.91; H 7.78; N 3.73.

TLC, Rf 0.40

HPLC, retention time 16.8 min.

Partricin methyl amide

TLC, Rf 0.45(A) and 0.40(B)

HPLC, retention time 32.1 min. (A) and 16.8 min. (B)

Partricin n-dodecyl amide

TLC, Rf 0.9 (A and B)

EXAMPLE 3

To a solution of 40 g of partricin A in 260 ml of dimethylacetamide, 6.1 g of 2-dimethylaminoethylamine are added under stirring, followed by dropwise adding 19.1 g of diphenyl phosphorazidate.

The exothermic reaction is moderated by cooling to 15° and stirred at the same temperature for 2 hours. At the end, further 6.1 g of 2-dimethylaminoethylamine and 19.1 g of diphenyl phosphorazidate, under cooling at 15°, are added. After 2 hours stirring, the reaction mixture is treated with 2.5 liters of water and the precipitate thereby formed is collected by filtration, thoroughly washed with 200 ml of ethanol and 800 ml of water, and dried at 50° under vacuum, thereby obtaining 42 g of crude product.

Small amounts of unreacted partricin A, if present at the TLC assay, are eliminated by dissolving the product into 1 liter of a methylene chloride:methanol 4:1, mixture, treating the solution with 40 g of Duolite LES resin under slow stirring overnight, and filtering off the resin.

The solution thereby obtained is then subjected to a column chromatography on silica gel 60, 70–230 mesh (400 g), eluting first with methylene chloride:methanol:water 72:24:4 and then with methylene chloride:methanol:water:triethylamine 72:24:4:4.

From the latter eluent, after TLC assay of the various fractions, there are obtained, by concentration under reduced pressure, 18 g of the expected partricin A 2-dimethylaminoethylamide as a yellow crystalline solid. The compound is then subjected to the suitable analytical assays according to the methods described in example 1.

Elem.Anal. for $C_{63}H_{96}N_4O_{18}$: Found %: C 63.23; H 8.11; N 4.66. Calc. %: C 63.19; H 8.08; N 4.68.

TLC, Rf 0.54

HPLC, retention time 30.4 min.

EXAMPLE 4

Operating essentially in accordance with the procedure of example 3, the following compounds have been prepared:

Partricin A 3-dimethylaminopropyl amide

Elem.anal.: for $C_{64}H_{98}N_4O_{18}$. Found %: C 63.82; H 8.11; N 4.58. Calc. %: C 63.45; H 8.15; N 4.62.

TLC, Rf 0.51

HPLC, retention time 30.6 min.

Partricin B 2-dimethylaminoethyl amide

Elem.anal.: for $C_{62}H_{94}N_4O_{18}$. Found %: C 63.51; H 8.15; N 4.68. Calc. %: C 62.92; H 8.01; N 4.73.

TLC, Rf 0.50

HPLC, retention time 20.6 min.

Partricin 3-dimethylaminopropyl amide

TLC, Rf 0.51 (A) and 0.48 (B)

HPLC, retention time 30.6 min. (A) and 16.0 min. (B)

EXAMPLE 5

Following essentially the same procedure as described in example 3, the derivatives described hereinafter have been obtained. The HPLS analyses (Hitachi L6200) have been carried out with the same solvent system and the same method as described in example 1, by using directly a linear gradient from 35% to 40% of acetonitrile for 35 min.

Partricin A 2-(N-pyrrolidino)ethyl amide

Elem.anal.: for $C_{65}H_{98}N_4O_{18}$. Found %: C 63.73; H 8.18; N 4.59. Calc. %: C 63.81; H 8.07; N 4.58.

TLC, Rf 0.61

HPLC, retention time 26 min.

Partricin A 2-(N-piperidino)ethyl amide

Elem.anal.: for $C_{66}H_{100}N_4O_{18}$. Found %: C 63.54; H 8.17; N 4.60. Calc. %: C 64.06; H 8.14; N 4.53.

TLC, Rf 0.66

HPLC, retention time 29 min.

Partricin A 2-(N-morpholino)ethyl amide

Elem.anal.: for $C_{65}H_{98}N_4O_{19}$. Found %: C 63.12; H 7.94; N 4.49. Calc. %: C 62.99; H 7.97; N 4.52.

TLC, Rf 0.61

HPLC, retention time 25 min.

Partricin A 3-(N-morpholino)propyl amide

Elem.anal.: for $C_{66}H_{100}N_4O_{19}$. Found %: C 62.80; H 7.98; N 4.49. Calc. %: C 63.24; H 8.04; N 4.47.

TLC, Rf 0.55

HPLC, retention time 26 min.

Partricin B 2-(N-piperidino)ethyl amide

Elem.anal.: for $C_{65}H_{98}N_4O_{18}$. Found %: C 63.93; H 8.10; N 4.55. Calc. %: C 63.81; H 8.07; N 4.58.

TLC, Rf 0.63

EXAMPLE 6

Operating essentially in accordance with the procedure of example 3, the following derivatives have been prepared:

Partricin A 2-(N'-methyl-N-piperazino)ethyl amide

Elem.anal.: for $C_{66}H_{101}N_5O_{18}$. Found %: C 63.36; H 8.17; N 5.60. Calc. %: C 63.29; H 8.13; N 5.59.

Partricin A 2-(N'-hydroxyethyl-N-piperazino)ethyl amide

Elem.anal.: for $C_{67}H_{103}N_5O_{19}$. Found %: C 62.70; H 8.09; N 5.44. Calc. %: C 62.74; H 8.09; N 5.46.

Partricin 2-(N'-methyl-N-piperazino)ethyl amide

EXAMPLE 7

Following essentially the same procedure as described in example 3, the following compounds have been obtained:

partricin A 2-(N-methyl-2-pyrrolidino)ethyl amide partricin A (N-ethyl-2-pyrrolidino)methyl amide partricin A 2-(2-pyridyl)ethyl amide partricin B 2-(N-methyl-2-pyrrolidino)ethyl amide

EXAMPLE 8

Following essentially the same procedures as described in examples 1-3, the following tertiary amides have been obtained:

partricin A N-methyl-N-2-(2-pyridyl)-ethyl amide partricin A N-methyl-N-(3-pyridyl)-methyl amide

EXAMPLE 9

Following the procedure described in example 3, the following tertiary amides have been obtained:

Partricin A pyrrolidide

Elem.anal.: for $C_{63}H_{93}N_3O_{18}$. Found %: C 63.76; H 7.90; N 3.58. Calc. %: C 64.10; H 7.94; N 3.56.

TLC, Rf 0.53

Partricin A piperidide

Elem.anal.: for $C_{64}H_{95}N_3O_{18}$. Found %: C 64.53; H 7.98; N 3.49. Calc. %: C 64.36; H 8.02; N 3.52.

TLC, Rf 0.58

Partricin A morpholide

Elem.anal.: for $C_{63}H_{93}N_3O_{19}$. Found %: C 63.65; H 7.88; N 3.48. Calc. %: C 63.24; H 7.83; N 3.51.

TLC, Rf 0.54

Partricin A N'-methyl-piperazide

Elem.anal.: for $C_{64}H_{96}N_4O_{18}$. Found %: C 63.82; H 8.14; N 4.60. Calc. %: C 63.56; H 8.00; N 4.63.

TLC, Rf 0.48

Partricin A N'-hydroxyethyl piperazide

Elem.anal.: for $C_{65}H_{98}N_4O_{19}$. Found %: C 63.21; H 7.98; N 4.55. Calc. %: C 62.99; H 7.97; N 4.52.

TLC, Rf 0.30

Partricin N'-methyl-piperazide

TLC, Rf 0.48 (A) and 0.45 (B)

EXAMPLE 10

1.2 g of partricin A 2-dimethylaminoethyl amide and 0.27 g of aspartic acid are suspended in 10 ml of distilled water and the mixture is kept under stirring for 10-15 minutes to complete dissolution.

The solution is then evaporated to dryness under vacuum and the residue is washed with ethanol and dried at 10 degrees under vacuum. Thus 1.4 g of partricin A 2-dimethylaminoethyl amide diaspartate, water-soluble, with slightly acidic reaction (pH 5 ca) are obtained. This compound shows the same characteristics as the free base in TLC (Rf 0.45) and HPLC (retention time 32.1 min).
Elem.anal. for $C_{71}H_{110}N_6O_{26}$: Found %: C 58.66; H 7.50; N 5.68. Calc. %: C 58.26; H 7.57; N 5.74.

EXAMPLE 11

A suspension of 12 g of partricin A 2-dimethylaminoethyl amide in 80 ml of water is treated with 2.7 g of aspartic acid, followed by stirring the mixture at room temperature until a solution is obtained (10–20 minutes). The solution thereby obtained is diluted with 800 ml of ethanol, thereby precipitating a yellow crystalline solid. After filtration, washing with ethanol and drying under vacuum at 50°, 14.3 g of partricin A 2-dimetilaminoethyl amide diaspartate are obtained, this product exhibiting the same phisico-chemical and analytical characteristics as the product obtained in example 10.

EXAMPLE 12

Operating in accordance with the procedure of example 10, the following compounds have been prepared:
Partricin A 2-dimethylaminoethyl amide diglutamate
Elem.anal.: for $C_{73}H_{114}N_6O_{26}$. Found. %: C 58.96; H 7.86; N 5.58. Calc. %: C 58.78; H 7.70; N 5.63.
Partricin A 2-dimethylaminoethyl amide diascorbate
Elem.anal.: for $C-75H_{112}N_4O_{30}$. Found. %: C 57.83; H 7.25; N 3.59. Calc. %: C 58.13; H 7.28; N 3.61.
Partricin A 2-dimethylaminoethyl amide diglucuronate
Elem.anal.: for $C_{75}H_{116}N_4O_{32}$. Found. %: C 57.02; H 7.36; N 3.52. Calc. %: C 56.81; H 7.37; N 3.53.
Partricin A 2-dimethylaminoethyl amide diglycolate
Elem.anal.: for $C_{67}H_{104}N_4O_{22}$. Found. %: C 60.78; H 7.98; N 4.25. Calc. %: C 61.08; H 7.96; N 4.25.
Partricin 2-dimethylaminoethyl amide diaspartate

EXAMPLE 13

Operating in accordance with the procedure of example 10, the following salts have been prepared:
Partricin A 2-(N-pyrrolidino)ethyl amide diaspartate
Elem.anal.: for $C_{73}H_{112}N_6O_{26}$. Found. %: C 58.77; H 7.50; N 5.64. Calc. %: C 58.86; H 7.58; N 5.64.
Partricin A 2-(N-piperidino)ethyl amide diaspartate
Elem.anal.: for $C_{74}H_{114}N_6O_{26}$. Found. %: C 59.43; H 7.62; N 5.61. Calc. %: C 59.11; H 7.64; N 5.59.
Partricin A 2-(N-morpholino)ethyl amide diaspartate
Elem.anal.: for $C_{73}H_{112}N_6O_{27}$. Found. %: C 58.45; H 7.54; N 5.56. Calc. %: C 58.23; H 7.50; N 5.58.
Partricin A 3-(N-morpholino)propyl amide diaspartate
Elem.anal.: for $C_{74}H_{114}N_6O_{27}$. Found. %: C 57.97; H 7.55; N 5.54. Calc. %: C 58.48; H 7.56; N 5.53.
Partricin B 2-(N-piperidino)ethyl amide diaspartate
Elem.anal.: for $C_{73}H_{112}N_6O_{26}$. Found. %: C 58.80; H 7.51; N 5.68. Calc. %: C 58.86; H 7.58; N 5.64.
Partricin A 2-(N'-methyl-N-piperazino)ethyl amide diaspartate
Elem.anal.: for $C_{74}H_{115}N_7O_{26}$. Found. %: C 58.60; H 7.71; N 6.48. Calc. %: C 58.52; H 7.63; N 6.46.
Partricin A 2-(N'-hydroxyethyl-N-piperazino)ethyl amide diglycolate
Elem.anal.: for $C_{71}H_{111}N_5O_{23}$. Found. %: C 60.85; H 7.93; N 4.98. Calc. %: C 60.80; H 7.98; N 4.99.
Partricin 2-(N'-methyl-N-piperazino)ethyl amide diglucuronate

EXAMPLE 14

Operating in accordance with the procedure of example 10, the following tertiary amide salts have been prepared:
Partricin A N'-methyl-piperazide diglucuronate
Elem.anal.: for $C_{76}H_{116}N_4O_{32}$. Found. %: C 57.40; H 7.36; N 3.54. Calc. %: C 57.13; H 7.32; N 3.51.
Particin A N'-hydroxyethyl-piperazide diglucuronate
Elem.anal.: for $C_{77}H_{118}N_4O_{33}$. Found. %: C 57.14; H 7.30; N 3.43. Calc. %: C 56.82; H 7.31; N 3.44.
Partricin N'-methyl-piperazide diaspartate

TABLE 1

| COMPOUND | MIC (mcg/ml) (a) candida albicans n. 37 (b) | (c) | IC50 (mcg/ml) (a) S. cerevisiae n. 167 (d) | MIC (mcg/ml) (a) T. vaginalis n. 6 (e) | EC (mcg/ml) (a) rat erythrocytes (f) |
|---|---|---|---|---|---|
| Partricin (P) | 0.040 | 0.034 | 0.005 | 0.250 | 0.3 |
| P. methy amide | 0.005 | 0.007 | 0.001 | 0.250 | 7.5 |
| P. n-dodecyl amide | 0.450 | 0.800 | 0.050 | >10 | >32 |
| P. 3-dimethyl-aminopropyl amide | 0.010 | 0.016 | 0.001 | 0.500 | 17 |
| Partricin A (P.A) | 0.038 | 0.040 | 0.004 | 0.250 | 0.3 |
| P.A methyl amide | 0.005 | 0.008 | 0.0007 | 0.250 | 8 |
| P.A ethyl amide | 0.009 | 0.010 | 0.001 | 0.500 | — |
| P.A n-propyl amide | 0.008 | 0.016 | 0.001 | 0.500 | — |
| P.A n-penthyl amide | 0.020 | 0.080 | 0.003 | 2.000 | — |
| P.A allyl amide | 0.006 | 0.010 | 0.0008 | 0.250 | — |
| P.A 2-dimethyl-aminoethyl amide | 0.002 | 0.008 | 0.0004 | 0.500 | 25 |
| P.A 3-dimethyl-aminopropyl amide | 0.003 | 0.008 | 0.0005 | 0.500 | 20 |
| P.A N'-methyl-piperazide | 0.001 | 0.004 | 0.0004 | 0.500 | — |
| Partricin B (P.B) | 0.040 | 0.040 | 0.005 | 0.250 | — |
| P.B methyl amide | 0.007 | 0.008 | 0.001 | 0.250 | — |
| P.B 2-dimethyl-aminoethyl- | 0.003 | 0.010 | 0.001 | 0.500 | — |

TABLE 1-continued

| COMPOUND | MIC (mcg/ml) (a) candida albicans n. 37 | | IC50 (mcg/ml) (a) S. cerevisiae n. 167 | MIC (mcg/ml) (a) T. vaginalis n. 6 | EC (mcg/ml) (a) rat erythrocytes |
|---|---|---|---|---|---|
| | (b) | (c) | (d) | (e) | (f) |
| amide | | | | | |

(a) Average of 2-5 experiments
(b) Sabouraud fluid medium, 24 hours at 36°
(c) Sabouraud fluid medium + agar, 24 hours at 36°
(d) PYG culture medium, 6 hours at 36°
(e) CPLM culture medium, 72 hours at 36°
(f) 2% suspension i BSA-Ringer, 1 hour at 36°

We claim:

1. A compound of the formula

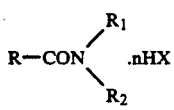

$$R-CON\begin{matrix}R_1\\ \\R_2\end{matrix} \cdot nHX \quad (I)$$

wherein:

R is the residue of partricin A or partricin B molecule, which is bound to the C-18 carboxyl;

$R_1$ is a dimethylamino-substituted cyclohexyl or phenyl group; or an alkyl group with 1 to 6 carbon atoms substituted with an N-methyl- or N-ethyl-cycloalkyleneamine with 4 to 5 carbon atoms, with a pyridyl group or with a primary amine group $NH_2$, a secondary amine group $NHR_3$ or a tertiary amine group $NR_3R_4$, wherein $R_3$ and $R_4$ are alkyl groups with 1 to 4 carbon atoms, or $NR_3R_4$ together form a basic nitrogen heterocycle, said heterocycle being 5- or 6-membered and optionally containing one or more further heteroatoms chosen from N or O or S;

$R_2$ is a hydrogen atom, a methyl group, or has the same meanings as $R_1$; or $NR_1R_2$ together form a basic nitrogen heterocycle, said heterocycle being 5- or 6-membered and optionally containing one or more further N atoms;

n is an integer of from 0 to 2,

X is the residue of a pharmacologically and pharmaceutically acceptable organic or inorganic acid.

2. A compound of formula (I) as claimed in claim 1, wherein the cycloalkyleneamine with 4 to 5 carbon atoms is the 2-pyrrolidino group.

3. A compound of formula (I) as claimed in claim 1, wherein the pyridyl group is 2- or 3-pyridyl.

4. A compound of formula (I) as claimed in claim 1, where $R_3$ and $R_4$ are methyl groups.

5. A compound of formula (i) as claimed in claim 1, where the $NR_3R_4$ group is N-pyrrolidino, N-piperidino, N-morpholino, N-piperazino, N'-methyl-N-piperazino, N'-hydroxyethyl-N-piperazino.

6. A compound of formula (I) as claimed in claim 1, where the $NR_1R_2$ group is N-pyrrolidino, N-piperidino, N-morpholino, N-piperazino, N'-methyl-N-piperazino, N'-hydroxyethyl-N-piperazino.

7. A compound of formula (I) as claimed in claim 1, where X is the residue of glucuronic, glycolic, aspartic or ascorbic acid.

8. A compound of formula (I) as claimed in claim 1 which is partricin A 2-(N-methyl-2-pyrrolidino)ethyl amide.

9. A compound of formula (I) as claimed in claim 1 which is partricin A 2-(2-pyridyl)ethyl amide.

10. A compound of formula (I) as claimed in claim 1 which is partricin A 2-dimethylaminoethyl amide.

11. A compound of formula (I) as claimed in claim 1 which is partricin A 3-dimethylaminopropyl amide.

12. A compound of formula (I) as claimed in claim 1 which is partricin A 2-(N-piperidino)ethyl amide.

13. A compound of formula (I) as claimed in claim 1 which is partricin A 2-(N'-methyl-N-piperazino)ethyl amide.

14. A compound of formula (I) as claimed in claim 1 which is partricin A pyrrolidide.

15. A compound of formula (I) as claimed in claim 1 which is partricin A morpholide.

16. A compound of formula (I) as claimed in claim 1 which is partricin A N'-methyl-piperazide.

17. A compound of formula (I) as claimed in claim 1 which is partricin A N'-hydroxyethyl piperazide.

18. A compound of formula (I) as claimed in claim 1 which is partricin A 2-dimethylaminoethyl amide diaspartate.

19. A compound of formula (I) as claimed in claim 1 which is partricin A 2-dimethylaminoethyl amide diascorbate.

20. A compound of formula (I) as claimed in claim 1 which is partricin A 2-dimethylaminoethyl amide diglucuronate.

21. A compound of formula (I) as claimed in claim 1 which is partricin A 3-dimethylaminopropyl amide diaspartate.

22. A compound of formula (I) as claimed in claim 1 which is partricin A 2-(N-pyrrolidino)ethyl amide diaspartate.

23. A compound of formula (I) as claimed in claim 1 which is partricin A N'-methylpiperazide diaspartate.

24. Pharmaceutical formulations against fungal and protozoan infections, for the treatment of hypercolesteraemia and hyperlipaemia conditions, of steroid hormones unbalances, of hypertrophic prostate and of lipid envelope virus infections, containing a therapeutically effective amount of one of the products of formula (I) according to claim 1, mixture with suitable, pharmaceutically acceptable excipients.

25. The compound of claim 1, wherein said further N atom in said basic nitrogen heterocycle formed by $NR_1R_2$ and $NR_3R_4$ is in the form of $N(CH_3)$ or $N(CH_2CH_2OH)$.

* * * * *